| United States Patent [19] | [11] Patent Number: 5,004,734 |
| Philippe et al. | [45] Date of Patent: Apr. 2, 1991 |

[54] DIAROMATIC ESTERS OF MACROLIDIC AND LINCOSAMIDIC ANTIBIOTICS AND PHARMACEUTICAL AND COSMETIC COMPOSITIONS CONTAINING THEM

[75] Inventors: Michel Philippe, Antony; Henri Sebag, Paris, both of France

[73] Assignee: Societe Anonyme Dite: L'Oreal, Paris, France

[21] Appl. No.: 266,597

[22] Filed: Nov. 3, 1988

[30] Foreign Application Priority Data

Nov. 4, 1987 [LU] Luxembourg ............................ 87039

[51] Int. Cl.$^5$ ...................... A61K 31/70; C07H 15/16; C07H 17/08

[52] U.S. Cl. ........................................ 514/29; 536/7.1; 536/7.2; 536/16.2; 514/24; 514/30; 514/844; 514/859

[58] Field of Search ....................... 536/7.1, 7.2, 16.2; 514/24, 29, 30, 844, 859

[56] References Cited

U.S. PATENT DOCUMENTS 4,575,497 3/1986 Omura et al. ...................... 514/30

OTHER PUBLICATIONS

European Search Report, Jun. 3, 1988.

*Primary Examiner*—Johnnie R. Brown
*Assistant Examiner*—Elli Peselev
*Attorney, Agent, or Firm*—Cushman, Darby & Cushman

[57] ABSTRACT

Diaromatic esters of macrolidic and lincosamidic antibiotics are employed in the treatment of acne.

9 Claims, No Drawings

DIAROMATIC ESTERS OF MACROLIDIC AND LINCOSAMIDIC ANTIBIOTICS AND PHARMACEUTICAL AND COSMETIC COMPOSITIONS CONTAINING THEM

The present invention relates to diaromatic esters of macrolidic and lincosamidic antibiotics, to a process for their preparation and to pharmaceutical and cosmetic compositions containing them for the treatment of various dermatoses, and principally in the treatment of acne.

More particularly, the esters in accordance with the present invention, are intended for the treatment of dermatoses, infectious or not.

In the treatment of acne, erythromycin among the macrolides as well as clindamycin among the lincosamides have been more particularly recommended, but their use requires (particularly for erythromycin) relatively high concentrations so as to obtain a satisfactory result.

Moreover, treatment with these antibiotics has proved, in certain cases, less effective, in the measure where certain strains of propionibacterium acnes have exhibited a progressive resistance in their regard.

The topical application of clindamycin and more particularly erythromycin collides, besides, with a problem of penetration through the corneum stratum limiting from this fact their efficacy.

The esters of antibiotics in accordance with the invention provide a satisfactory solution to the problem raised by the use of these antibiotics in the treatment of acne, in the measure where it is established that these esters have an activity on propionibacterium acnes, the main germ responsible for the inflammation phenomena of the skin.

The diaromatic esters in accordance with the invention have from the fact of their structure a pronounced lipophilic character which facilitates a better penetration across the epidermis.

The new esters in accordance with the invention are well tolerated by the skin and are revealed to be much less toxic when taken orally than the antibiotic/acid combination.

Besides, they exhibit, with respect to known esters, the advantage of possessing a potential comedolytic activity due to the corresponding acid chain, which confers to these esters an image of a "prodrug".

The state of the art relative to esters of macrolides is represented principally by French patent No. 85.07287 (2.582.000) which relates to poly unsaturated fatty esters of erythromycin A such as the linoleate, and the linolenate of erythromycin A.

The state of the art relative to esters of lincosamides is represented principally by German patent No. 2.017.003 which describes the preparation of esters of lincomycin and clindamycin whose acyl chain has between 1 and 18 carbon atoms.

The present invention relates to as a new industrial product, diaromatic esters of macrolides or lincosamides, said esters having the following general formula:

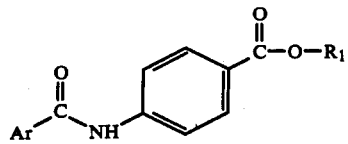

wherein
$R_1$ represents a macrolide or lincosamide radical,
Ar represents an aromatic radical having one of the following formulas:

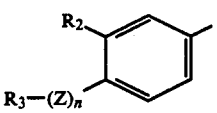

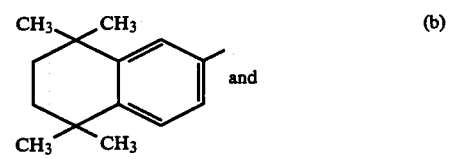

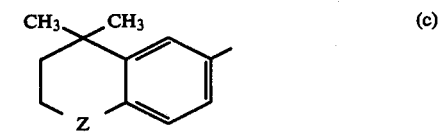

wherein
n is 0 or 1,
$R_2$ and $R_3$ represent hydrogen, linear or branched alkyl having 1–15 carbon atoms or cycloalkyl having 5–10 carbon atoms, and
Z is an atom of oxygen or sulfur, and
the mixtures and salts of said esters.

Representative cycloalkyls having 5–10 carbon atoms include cyclopentyl, cyclohexyl, 1-methyl cyclohexyl and 1-adamantyl.

Representative macrolides include erythromycin A, roxithromycin, oleandomycin, josamycin and spiramycines I, II and III.

Representative lincosamides include lincomycin and clindamycin.

A—The esters of erythromycin A and roxithromycin can be represented by the formula

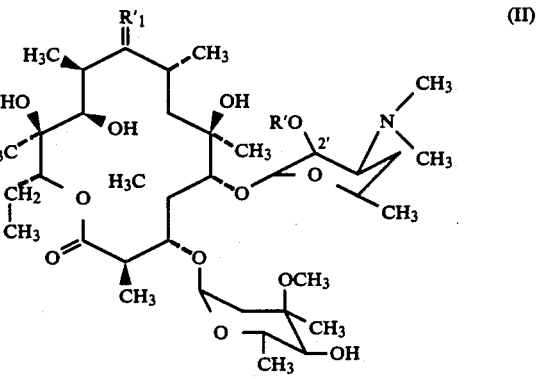

wherein
$R'_1$ represents O (erythromycin A) or N~O-CH$_2$-O-CH$_2$-CH$_2$-O-CH$_3$ (roxithromycin), and
R' represents the following acyl radical:

(I')

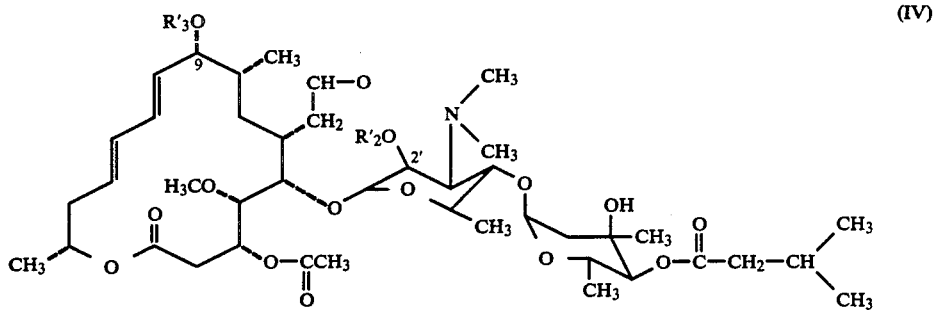

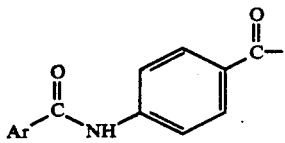

wherein
Ar has the same meaning given above.

These esters of erythromycin A and roxithromycin are those in position 2'.

B—The esters of oleandomycin can be represented by the following formula:

(III)

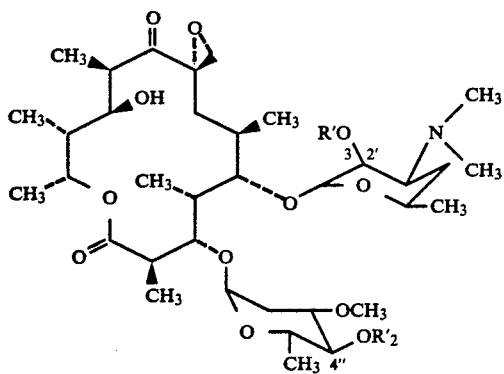

wherein
R'$_2$ and R'$_3$ represents R' or hydrogen with the proviso that at least one of R'$_2$ and R'$_3$ represents R', and
R' has the same meaning given above.

These esters are those in position 2' and/or 4", but they can be provided in the form of a mixture.

C—The esters of josamycin can be represented by the following formula:

(IV)

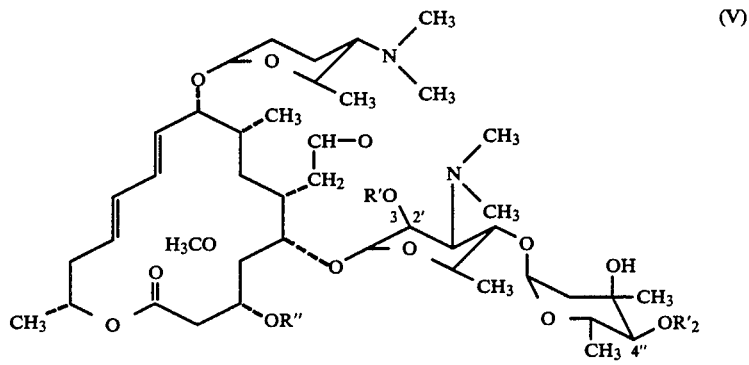

wherein
R'$_2$ and R'$_3$ represent R' or hydrogen with the proviso that at least one of R'$_2$ and R'$_3$ represents R' and R' has the same meaning given above.

These esters are those in position 9 and/or 2', but they can be provided in the form of a mixture.

D—The esters of spiramycins can be represented by the following formula:

(V)

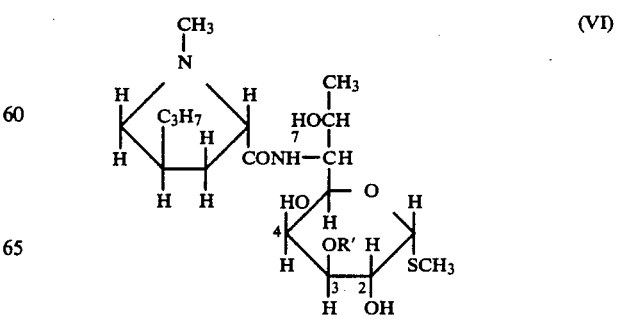

wherein
R'$_2$ or R'$_3$ represents R' or hydrogen with the proviso that at least one of R'$_2$ and R'$_3$ represents R' and R' has the same meaning given above and
R" represents hydrogen (spiramycin I), acetyl (spiramycin II) or propionyl (spiramycin III).

These esters of spiramycin (I), (II) and (III) are those in position 2' and/or 4 and they can be provided in the form of a mixture.

E—The esters of lincomycin and clindamycin can be represented, respectively, by the following formulas (VI) and (VII):

(VI)

-continued

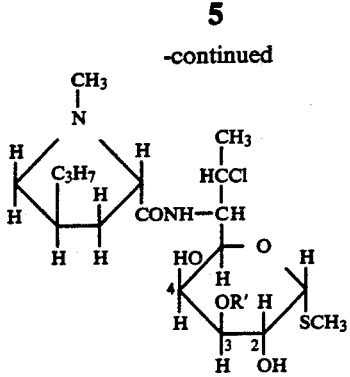
(VII)

wherein
R' has the same meaning given above.

The esters of lincomycin (VI) and clindamycin (VII) are preferably those in position 3. However, they can be provided in the form of mixtures with the esters in position 2, 4 and 7 of lincomycin and with esters in position 2 and 4 of clindamycin.

Representative diaromatic esters of formula I, in accordance with the invention, include the following:

2'-O-[4-[3-(1-adamantyl)-4-methoxy benzamido]-benzoyl] erythromycin A,
3-O-[4-[3-(1-adamantyl)-4-methoxy benzamido]benzoyl]clindamycin,
2'-O-[4-[3-(1-adamantyl)-4-methoxy benzamido]-benzoyl] roxithromycin,
9-O-[4-[3-(1-adamantyl)-4-methoxy benzamido]-benzoyl] josamycin and its 2' position isomer,
3-O-[4-[3-(1-adamantyl)-4-hydroxy benzamido]-benzoyl] clindamycin,
2'-O-[4-[3-(1-methyl cyclohexyl)-4-methoxy benzamido]benzoyl] oleandomycin,
9-O-[4-[3-(1-adamantyl)-4-decyloxy benzamido]-benzoyl] josamycin and its 2' position isomer,
2'-O-[4-[3-(1-adamantyl)-4-hexyloxy benzamido]benzoyl]spiramycin (I), (II) and (III),
2 -O-[4-[3-(1,1-dimethyl decyl)-4-methoxy benzamido]-benzoyl]erythromycin A,
2'-O-[4-(3-tert. butyl-4-methoxy benzamido) benzoyl] roxithromycin, and
3-O-[4-(5,6,7,8-tetrahydro-5,5,8,8-tetramethyl-2-naphthamido) benzoyl] lincomycin.

The present invention also relates to a process for preparing the diaromatic esters of antibiotics of formula (I) according to the present invention.

Various procedures for esterification can be employed, but preferably this esterification is carried out in an anhydrous organic solvent medium, preferably in tetrahydrofuran alone or in mixture with another organic solvent such as pyridine, by reacting an excess of mixed anhydride of the formula:

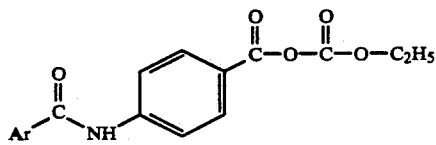

wherein
Ar has the same meaning given above,
the said anhydride being prepared in situ, (for example starting with ethyl chloroformate and the corresponding acid) with a macrolide or lincosamide in base form, in the presence of an organic or mineral base such as pyridine and/or sodium bicarbonate and/or triethylamine.

This method with mixed anhydride permits to obtain preferentially esters in position 2' of macrolides and/or in position 9 principally for josamycin and/or in position 4" principally for the spiramycins and the esters in position 3 of lincosamides in good yield conditions.

The other procedures of esterification principally of lincomycin and clindamycin by the method using imidazolides of corresponding acids in an anhydrous solvent such as N,N-dimethylformamide in the presence of a base such as sodium or potassium tert. butylate lead to a mixture of esters of these antibiotics.

The present invention also relates to pharmaceutical compositions that can be administered topically, orally, parenterally or rectally as well as to cosmetic compositions for the treatment of various dermatoses, principally acne. These compositions can be provided in anhydrous form and contain at least one ester in accordance with the invention, such as defined above, in an amount ranging from 0.001 to 10 weight percent, but preferably from 0.01 to 1 weight percent, based on the total weight of the composition.

For the preparation of compositions, according to the invention, containing as the active component, at least one ester according to the invention such as defined above, there can be employed vehicles and adjuvants described in the literature for pharmaceuticals, cosmetics and related fields.

For the preparation of solutions, there can be employed, for example, an acceptable organic solvent from a physiologic view point. The acceptable organic solvent is selected principally from the group consisting of acetone, isopropyl alcohol, triglycerides of fatty acids, $C_1-C_4$ alkyl esters of short chain acids, polytetrahydrofuran ethers and silicones such as cyclomethicones.

The compositions according to the invention can also include a thickening agent such as a cellulose derivative in an amount ranging from 0.5 to 20 weight percent based on the total weight of the composition.

The compositions according to the invention can also contain in combination with at least one ester according to the invention, at least one other known anti-acne agent.

If necessary, a conventional adjuvant selected from the group consisting of antioxidants, preservatives, perfumes and dyes can be added.

Representative useful antioxidants include, for instance, t-butylhydroxy quinone, butylhydroxy anisole, butylhydroxy toluene and α-tocopherol and its derivatives.

The pharmacologic and galenic transformations of the compounds of the present invention are effected in a known manner.

The galenic forms can be, for topical applications, creams, milks, gels, more or less thick lotions, lotion-impregnated pads, pomades, sticks or even aerosol formulations provided in the form of sprays or foams.

The compositions for oral administration can be provided in the form of tablets, gelules, lozenges, syrups, suspensions, emulsions, powders, granules or solutions.

The compositions can also be provided in the form of suppositories.

The treatment of acne using the topical compositions of the invention comprises applying, two or three times each day, a sufficient amount on the areas of the skin being treated and this for a period of time ranging from 6 to 30 weeks and preferably from 12 t 24 weeks.

The compositions according to the invention can also be used as a preventative, i.e. on the areas of the skin susceptible of being attacked by acne.

There are now given, as an illustration, several examples of the preparation of diaromatic esters of antibiotics in accordance with the invention as well as several examples of pharmaceutical or cosmetic compositions for the treatment of dermatoses, principally of acne.

EXAMPLE 1

Preparation of 2'-O-[4-[3-(1-adamantyl)-4-methoxy benzamido]-benzoyl] erythromycin A In a round bottom flask, under an inert atmosphere, there are dissolved 6.7 g (16.6. mmoles) of 4-[3-(1-adamantyl)-4-methoxy benzamido] benzoic acid in 35 ml of anhydrous tetrahydrofuran; the reaction mixture is cooled to 0° C, and there are then added 2.3 ml of triethylamine and 1.6 ml (16.6 mmoles) of ethyl chloroformate. The solution is stirred for 5 minutes, and there are added 20 ml of anhydrous pyridine, and then 4.9 g (6.7 mmoles) of erythromycin A previously dissolved in 150 ml of tetrahydrofuran. The reaction mixture is stirred for 10 hours and the temperature is permitted to return to ambient temperature (chromatography on thin layer silica gel: methylene chloride (90)/methanol (10)). The solution is poured into 60 ml of water and extracted with ethyl acetate. The organic phase is dried on magnesium sulfate, filtered, and then concentrated under a partial vacuum. The crude product thus obtained is chromatographed on a silica gel column (HPLC) by using as the eluant: ethyl acetate (7)/hexane (3) to result in the isolation of 4.5 g (60% yield) of 2'-O-[4-[3-(1-adamantyl)-4-methoxy benzamido]-benzoyl] erythromycin A.

M.P. = 138° C. (hexane/ethyl acetate)
$[\alpha]_D^{22} = -62°$ (C=3 mg./ml-dichloromethane).
Microanalysis: $C_{62}H_{92}N_2O_{16} \cdot 4H_2O$; M.W. = 1193.5

|  | C | H | N |
|---|---|---|---|
| Calculated, % | 62.39 | 8.44 | 2.34 |
| Found, % | 62.44 | 8.48 | 1.95 |

NMR $_{13}$C (CDCl$_3$, internal ref. T.M.S.)

Negative γ effects in 1' (−2.2 ppm) and 3' (−2.3 ppm) indicate the position of the ester at the 2' position.

EXAMPLE 2

Preparation of 2'-O-[4-[3-(1-adamantyl)-4-methoxy benzamido]-benzoyl] roxithromycin In a round bottom flask, under an inert atmosphere, there are dissolved 700 mg (1.72 mmoles) of 4-[3-(1-adamantyl)-4-methoxy benzamido] benzoic acid in 20 ml of anhydrous tetrahydrofuran; the reaction mixture is cooled to 0° C., and there are then added 0.240 ml of thriethylamine and 0.17 ml (1.75 mmole) of ethyl chloroformate; the solution is stirred for 1 hour, and there are added 0.3 ml of anhydrous pyridine, then 570 mg (0.7 mmole) of roxithromycin previously dissolved in 20 ml of tetrahydrofuran The reaction mixture stirred for 10 hours and the temperature is permitted to return to ambient temperature (chromatography on thin layer silica gel: methylene chloride 90%/methanol 10%.

The solution is poured into 40 ml of water and then extracted with ethyl acetate. The organic phase is dried on magnesium sulfate, filtered, and then concentrated under a partial vacuum. The crude product thus obtained is chromatographed on a silica gel column (HPLC) by using as the eluant: ethyl acetate (7)/hexane (3) to result in the isolation of 2'-O-[4-[3-(1-adamantyl)-4-methoxy benzamido]benzoyl]roxithromycin.

M.P. = 137° C. (ethyl acetate/heptane)
$[\alpha]_D^{20} = -71°$ (C=2 mg/ml-dichloromethane)
Microanalysis: $C_{67}H_{103}N_3O_{18} \cdot 6H_2O$; M.W. = 1346.6

|  | C | H | N |
|---|---|---|---|
| Calculated, % | 59.76 | 8.60 | 3.11 |
| Found, % | 59.31 | 7.99 | 2.84 |

NMR $^{13}$C (CDCl$_3$, internal ref. T.M.S.)

Negative effects in 1'(−2.7 ppm) and 3' (−2.5 ppm) indicate the position of the ester at the 2' position.

In accordance with the same operating procedures described above in Examples 1 and 2, the other esters listed above have also been prepared.

Pharmaceutical and Cosmetic Compositions

| A. Gel for the topical treatment of acne | |
|---|---|
| 1. Hydroxypropyl cellulose | 1 g |
| Butylhydroxy toluene | 0.05 g |
| 2'-O-[4-[3-(1-adamantyl)-4-methoxy benzamido]-benzoyl] erythromycin A | 0.3 g |
| Isopropanol, sufficient amount for | 100 g |
| 2. Hydroxypropyl cellulose | 1 g |
| Butylhydroxy toluene | 0.05 g |
| 2'-O-[4-[3-(1-adamantyl)-4-methoxy benzamido]benzoyl] roxithromycin | 0.5 g |
| Isopropanol, sufficient amount for | 100 g |
| B. Lotion for the topical treatment of acne | |
| 1. Butylhydroxy toluene | 0.05 g |
| 2'-O-[4-[3-(1-adamantyl)-4-methoxy benzamido]benzoyl erythromycin A | 1 g |
| Triglycerides of $C_8$–$C_{12}$ fatty acids, sufficient amount for | 100 g |
| 2. Butylhydroxy toluene | 0.05 g |
| 2'-O-[4-[3-(1-adamantyl)-4-methoxy benzamido]benzoyl] roxithromycin | 1 g |
| Isopropanol | 30 g |
| Triglycerides of $C_8$–$C_{12}$ fatty acids, sufficient amount for | 100 g |
| C. Stick for the topical treatment of acne | |
| 1. White petrolatum | 52 g |
| Petrolatum oil | 15 g |
| Refined paraffin | 32 g |
| 2'-O-[4-[3-(1-adamantyl)-4-methoxy benzamido]benzoyl] erythromycin A | 1 g |
| 2. White petrolatum | 52 g |
| Petrolatum oil | 15 g |
| Refined paraffin | 32 g |
| 2'-O-[4-[3-(1-adamantyl)-4-methoxy benzamido] benzoyl] roxithromycin | 1 g |

What is claimed is:

1. A diaromatic ester of a macrolide or lincosamide having the formula

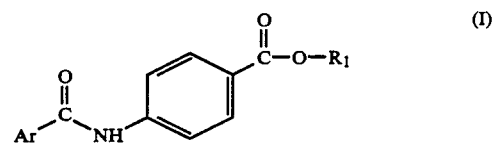

(I)

wherein

R₁ represents a macrolide selected from the group consisting of:
erythromycin A substituted in the 2' position,
roxithromycin substituted in the 2' position,
oleandomycin substituted in the 2' position,
oleandomycin substituted in the 4" position,
oleandomycin substituted in the 2' and 4" positions.
josamycin substituted in the 9 position,
josamycin substituted in the 2' position,
josamycin substituted in the 9 and 2' positions,
spiramycin (I) substituted in the 2' position,
spiramycin (I) substituted in the 4" position,
spiramycin (I) substituted in the 2' and 4" positions,
spiramycin (II) substituted in the 2' position,
spiramycin (II) substituted in the 4" position,
spiramycin (II) substituted in the 2' and 4" positions,
spiramycin (III) substituted in the 2' position,
spiramycin (III) substituted in the 4" position,
spiramycin (III) substituted in the 2' and 4" positions,
or R₁ represents a lincosamide selected from the group consisting of:
lincomycin substituted in the 3 position,
clindamycin substituted in the 3 position,
lincomycin substituted in the 2, 4 and 7 positions and
clindamycin substituted in the 2 and 4 positions,
Ar represents an aromatic radical selected from

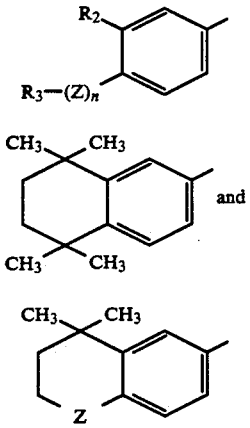

wherein
n is 0 or 1,

R₂ and R₃ represent hydrogen, linear or branched alkyl having 1-15 carbon atoms or cycloalkyl having 5-10 carbon atoms, and
Z is an atom of oxygen or sulfur,
and mixtures and salts of said esters.

2. The ester of claim 1 selected from the group consisting of
2'-O-[4-[3-(1-adamantyl)-4-methoxy benzamido]-benzoyl] erythromycin A,
3-O-[4-[3-(1-adamantyl)-4-methoxy benzamido]benzoyl]clindamycin,
2'-O-[4-[3-(1-adamantyl)-4-methoxy benzamido]-benzoyl] roxithromycin,
9-O-[4-[3-(1-adamantyl)-4-methoxy benzamido]-benzoyl] josamycin and its 2' position isomer,
3-O-[4-[3-(1-adamantyl)-4-hydroxy benzamido]-benzoyl] clindamycin,
2'-O-[4-[3-(1-methyl cyclohexyl)-4-methoxy benzamido]benzoyl] oleandomycin,
9-O-[4-[3-(1-adamantyl)-4-decyloxy benzamido]-benzoyl] josamycin and its 2' position isomer,
2'-O-[4-[3-(1-adamantyl)-4-hexyloxy benzamido]benzoyl]spiramycin (I), (II) and (III),
2'-O-[4-[3-(1,1-dimethyl decyl)-4-methoxy benzamido]-benzoyl]erythromycin A,
2'-O-[4-(3-tert. butyl-4-methoxy benzamido) benzoyl] roxithromycin, and 3. A pharmaceutical or cosmetic composition for the treatment of dermatoses comprising in an anhydrous vehicle, as the active component, a pharmaceutically or cosmetically effective amount of at least one ester of claim 1.

4. The composition of claim 3 wherein said ester is present in an amount ranging from 0.001 to 10 weight percent based on the total weight of said composition.

5. The composition of claim 3 wherein said ester is present in an amount ranging from 0.01 to 1 weight percent based on the total weight of said composition.

6. The composition of claim 3 wherein said anhydrous vehicle is acetone, isopropyl alcohol, triglycerides of fatty acids, C₁-C₄ alkyl ester of a short chain acid, poly tetrahydrofuran ether, a silicone or a mixture thereof.

7. The composition of claim 3 which also contains a thickening agent in an amount ranging from 0.5 to 20 weight percent based on the total weight of said composition.

8. The composition of claim 7 wherein said thickening agent is a cellulose derivative.

9. The composition of claim 3 which also contains one or more of an antioxidant, a preservative, a perfume, a colorant or another anti-acne agent.

* * * * *